(12) United States Patent
Gunawardana

(10) Patent No.: US 7,113,051 B2
(45) Date of Patent: Sep. 26, 2006

(54) FREQUENCY CHARACTERIZATION OF QUARTZ CRYSTALS

(75) Inventor: Ruvinda Gunawardana, Sugar Land, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 129 days.

(21) Appl. No.: 10/707,723

(22) Filed: Jan. 7, 2004

(65) Prior Publication Data

US 2005/0146244 A1   Jul. 7, 2005

(51) Int. Cl.
*H03L 1/00* (2006.01)

(52) U.S. Cl. .................. 331/176; 331/158; 331/116 R; 331/116 FE; 331/66

(58) Field of Classification Search ................ 331/158, 331/66, 176, 116 R, 116 FE
See application file for complete search history.

(56) References Cited

U.S. PATENT DOCUMENTS

| | | | |
|---|---|---|---|
| 3,619,806 A | 11/1971 | Phillips | 331/69 |
| 4,079,280 A | 3/1978 | Kusters et al. | 310/318 |
| 4,084,131 A | 4/1978 | Matthey | 324/727 |
| 4,380,745 A | 4/1983 | Barlow et al. | 331/176 |
| 4,412,172 A | 10/1983 | Vig | 324/727 |
| 4,427,952 A | 1/1984 | Zumsteg | 331/176 |
| 4,586,006 A | 4/1986 | Emmons | 331/69 |
| 4,746,879 A | 5/1988 | Ma et al. | 331/44 |
| 4,918,372 A | 4/1990 | Filler et al. | 324/727 |
| 4,922,212 A | 5/1990 | Roberts et al. | 331/176 |
| 5,081,431 A | 1/1992 | Kubo et al. | 331/158 |
| 5,170,136 A | 12/1992 | Yamakawa et al. | 331/176 |
| 5,180,942 A | 1/1993 | Marvin et al. | 310/346 |
| 5,214,668 A | 5/1993 | Satou et al. | 374/117 |
| 5,473,289 A | 12/1995 | Ishizaki et al. | 331/176 |
| 5,525,936 A | 6/1996 | Post et al. | 331/47 |
| 5,668,506 A | 9/1997 | Watanabe et al. | 331/66 |
| 5,729,181 A | 3/1998 | Cutler et al. | 331/69 |
| 5,917,272 A | 6/1999 | Clark et al. | 310/343 |
| 6,127,661 A * | 10/2000 | Fry | 219/497 |
| 6,606,009 B1 | 8/2003 | Gunawardana et al. | 331/176 |
| 2002/0005765 A1 | 1/2002 | Ashley et al. | 331/176 |
| 2003/0184399 A1 | 10/2003 | Lanque et al. | 331/176 |

FOREIGN PATENT DOCUMENTS

GB    2 064 248 A    6/1981

* cited by examiner

*Primary Examiner*—Arnold Kinkead
(74) *Attorney, Agent, or Firm*—Victor H. Segura; Brigitte L. Echols; Dale V. Gaudier

(57) ABSTRACT

Techniques for determining a frequency profile of a quartz crystal in real time. Quartz crystals are subjected to a series of temperature cycles at various temperature rates and the crystal frequencies, crystal temperature parameters, and the temperature rates are monitored as the crystal is subjected to the temperature cycles. The monitored frequencies are grouped correlated with the monitored temperature parameters and temperature rates. A system for determining the frequency of a quartz crystal includes a processor adapted to perform the frequency profiling techniques.

31 Claims, 6 Drawing Sheets

FREQUENCY CHARACTERIZATION OF QUARTZ CRYSTALS

BACKGROUND OF INVENTION

1. Field of the Invention

The invention relates generally to the field of quartz crystals used as highly stable frequency standards (such as clocks). More particularly, the invention relates to techniques for profiling or characterizing the frequency output of crystal-based oscillators with reduced deviations in frequency due to environmental effects.

2. Background Art

Timing of operation of electronic devices, particularly digital devices, requires an accurate, frequency stable clock signal. Many such electronic devices are subjected to variations in ambient temperature during their operation. As is well known in the art, changes in ambient temperature affect the frequency of a typical crystal.

While quartz oscillators are considerably more stable when compared to other types of oscillators, their frequency output is known to exhibit some drift under rapid temperature variations. The effect of stresses on quartz crystals is well known and exploited in the design of quartz based stress and pressure sensors. Due to the low thermal conductivity and the anisotropic properties of quartz, heating and cooling crystals is known to cause stresses in the crystal, which affects the frequency. See, Bottom, Virgile E. *Introduction to Quartz Crystal Unit Design,* New York: D. Van Nostrand, 1982. For this reason, it is generally not recommended to subject quartz crystals to rapid temperature gradients.

In conventional applications the frequency deviations of quartz crystals due to temperature are profiled or characterized during manufacture and compensated for in real time. Rapid temperature fluctuations in the crystal's environment and changing temperature rates, also referred to as temperature gradients, cause the crystal frequency to deviate from the characterization. Though the varying temperature rates may last for a brief period, their effects can last for long periods of time, causing measurement errors.

In order to achieve greater frequency stability, several methods have been proposed to account for these deviations. One approach is to place the crystal in a temperature controlled chamber, which will keep the crystal at a constant temperature and prevent any deviation in frequency. See, for example, U.S. Pat. Nos. 5,917,272, 5,729,181, 5,180,942, 4,586,006 and 3,619,806. Another approach taken to compensate for the deviations in frequency due to temperature is to use a voltage-controlled oscillator of which the frequency can be adjusted by changing the voltage at the control input. In these designs, the temperature at the crystal is measured and used to digitally compute a correction voltage to be applied to the voltage-controlled oscillator. See, for example, U.S. Pat. Nos. 5,668,506, 5,473,289, 5,214,668, 5,170,136, 5,081,431, 4,922,212, 4,746,879, 4,427,952 and 4,380,745.

One problem with using a temperature sensor and measuring the temperature outside the crystal is that there is a time lag between the actual crystal temperature (at the quartz plate) and the outside where the temperature is measured. This causes the oscillators to be slow in responding to a change in temperature, introducing errors. A proposed solution to this problem is to have the crystal oscillate in two modes simultaneously, where one of the two modes is temperature sensitive while the second mode is relatively stable with temperature. The temperature sensitive mode is used to obtain the temperature at the crystal itself and then used to compensate for minor deviations with temperature in the stable mode. See, for example, U.S. Pat. Nos. 5,525,936 and 4,079,280. In spite of the very accurate measurement of temperature in these designs, high temperature gradients in the environment still introduce errors. Modern crystals are also cut at special angles, such as the SC cut, in an attempt to minimize frequency deviation due to temperature.

Another method that can be used to minimize problems due to fluctuating temperature rates is to place the crystal in a temperature controlled chamber. See, for example, U.S. Pat. No. 6,606,009 (assigned to the present assignee). However, this option entails higher power consumption, which can be a disadvantage in certain applications. Thus a need remains for improved techniques to account for and minimize frequency deviation in crystal-based oscillators due to environmental variations.

SUMMARY OF INVENTION

An aspect of the invention provides a method for determining a frequency profile of a quartz crystal. The method comprises subjecting the quartz crystal to temperature cycles at various temperature rates; monitoring the crystal frequencies, a crystal temperature parameter, and the temperature rates as the crystal is subjected to the temperature cycles; and grouping the monitored frequencies correlated with the monitored temperature parameters and temperature rates.

An aspect of the invention provides a method for determining a frequency of a quartz crystal. The method comprises subjecting the quartz crystal to temperature cycles at various temperature rates; monitoring the crystal frequencies, a crystal temperature parameter, and the temperature rates as the crystal is subjected to the temperature cycles; grouping the monitored frequencies correlated with the temperature parameters and temperature rates; determining the temperature and a temperature rate of the crystal; and relating the determined crystal temperature and temperature rate to the grouped frequencies to determine the crystal frequency.

An aspect of the invention provides a method for determining a frequency of a quartz crystal. The method comprises determining a temperature of the quartz crystal; deriving a temperature rate from the determined crystal temperature; and relating the crystal temperature and temperature rate to a data set characterizing a correlation between the crystal frequency, temperature, and temperature rates to determine the crystal frequency.

An aspect of the invention provides a system for determining a frequency of a quartz crystal. The system comprises a crystal having a frequency output related to a temperature of the crystal; and a processor adapted to calculate a crystal frequency from a measured temperature parameter of the crystal, a temperature rate of the crystal, and observed frequencies of the crystal correlated with observed temperature parameters and temperature rates of the crystal.

BRIEF DESCRIPTION OF DRAWINGS

Other aspects and advantages of the invention will be apparent from the following description and the appended claims.

DETAILED DESCRIPTION

In quartz crystal oscillator applications that require significant frequency stability, the temperature dependency of the frequency is typically profiled or characterized during manufacturing and captured in the form of a polynomial or look up table. During characterization, a crystal is subjected to a temperature cycle while the frequency and temperature are monitored. A temperature cycle involves heating from the lowest to highest operating temperature and then cooling down from highest to lowest temperature. The repeatability of the crystal frequency response is crucial to the success of high stability applications. If the crystal were perfect, the frequency response during heating would theoretically match perfectly with the frequency response during cooling. In reality, however, a crystal's responses do not match perfectly. This effect, sometimes referred to as hysteresis, causes the response during heating to be slightly different from that during cooling. This effect is referred to as temperature rate/gradient effects in this disclosure as a strong dependency of this effect on the rate of heating or the temperature rate has been observed.

Figure 1:
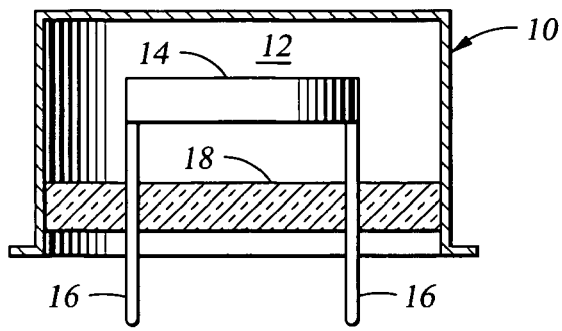
FIG. 1 is a cross-section of a quartz crystal package in accord with the invention.

An example of a basic quartz crystal device that may be used to implement various aspects of the invention is shown generally in FIG. 1. A quartz plate or disc 14 is attached to mounting clips/electrical leads 16. The disc 14 is disposed within a housing 10 and sealed therein by an insulating layer 18 (e.g. glass layer). The housing 10 is preferably evacuated to form a vacuum area 12 for the quartz disc 14 and surroundings. Electrical connections to electrodes on the disc 14 are made via the leads 16 passing through the insulating layer 18. Although FIG. 1 shows one sample quartz crystal device, it will be appreciated by those skilled in the art that there are many standard package styles/configurations used in mounting quartz crystals. Further description of quartz crystal packages is found in Griffith, James E., "Development And Advancements in SC-Cut Crystals", RF Expo EAST, 1994, (http://www.corningfrequency.com).

Figure 2:
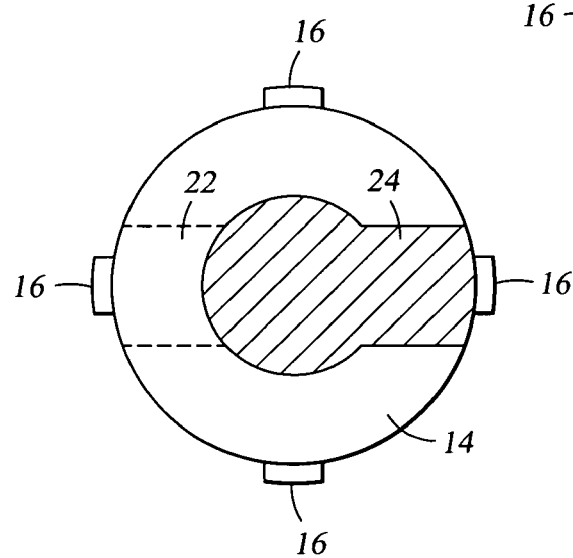
FIG. 2 is an overhead detailed view of the quartz crystal of FIG. 1.

FIG. 2 shows a more detailed view of the quartz disc 14 as viewed from above. The disc 14 has two metal electrodes, one electrode 24 on the top surface and the other 22 on the bottom surface, to provide the electrical stimulus to make the disc vibrate. The electrodes 22, 24 are disposed on the disc 14 by means well known in the art. The disc 14 housing 10 is metallic, which is typical for conventional crystal packages.

When one considers the characterization cycle where the crystal is heated, one can expect the metal housing 10 to heat first and then the disc 14. In this situation, since the area inside the housing 10 is a vacuum, the strongest heat flow is expected through the mounting clips/leads 16 connected to the electrodes 22, 24 as they are made of metal, which conducts heat well. Therefore, when one considers the temperature distribution of the quartz disc 14, one can expect the immediate areas close to the connected leads 16 to get hotter while areas further away from the leads remain relatively cooler since quartz is generally a poor heat conductor. Note that the mounting clips 16 not used as leads for the electrodes 22, 24 may be non-metallic in some designs. One can expect the hottest disc 14 areas to expand most due to thermal expansion and the colder areas to expand less. This type of mismatch in expansion is likely to induce mechanical stresses, causing changes in the vibrating frequency.

During the cooling part of the cycle, the housing 10 exterior is colder relative to the disc 14 and heat flows in the opposite direction through the leads 16. Thus in this situation, the area further away from the leads 16 will be hot and expanded while the area closer to the leads will be cooler and contracting. This reversal in stress states affects the crystal, causing frequency shifting in one direction during heating and in the opposite direction during cooling. These stresses induced by non-uniform temperature distributions are key factors in quartz crystal frequency shifts, producing frequency gradient effects.

As previously discussed, conventional methods of compensating for deviations in quartz oscillator frequency output due to temperature are characterized as $$f=f(T), \quad (1)$$

where f represents frequency and T the temperature. Manufactured crystals are subjected to a temperature cycle while the frequency and temperature are measured. This data is used to compute Equation (1) by optimization. This function is typically represented as a polynomial:

$$f(T) = \sum_{i=0}^{n} a_i T^i, \quad (2)$$

and the coefficients are computed by optimization (polynomial fit to the data) using the characterization data. These coefficients are typically stored and used to compute the actual frequency of the oscillator by measuring the temperature.

Techniques of the present invention account for temperature gradient effects on the crystal by performing a two-dimensional characterization where the two dimensions are a temperature parameter and temperature rate. The temperature parameter may be any parameter representative of temperature. In one embodiment the temperature parameter is the ratio of frequencies (Fb/Fc) as described in U.S. Pat. No. 6,606,009 (incorporated herein in its entirety by reference), with the temperature rate being captured by the time derivative of the parameter. In one process of the invention, the characterization involves subjecting the quartz crystal 14 to multiple temperature cycles with varying temperature rates. The crystal frequency is then characterized as a function of both the temperature parameter and temperature rate as follows:

$$f = f(T, \dot{T}), \dot{T} = \frac{dT}{dt}, \quad (3)$$

where f represents frequency, T represents the temperature or any parameter representing temperature, $\dot{T}$ represents a time derivative of T, and t represents time. The characterization can be represented by a polynomial or look up table which may be used in real time to compute the crystal frequency.

Figure 3:
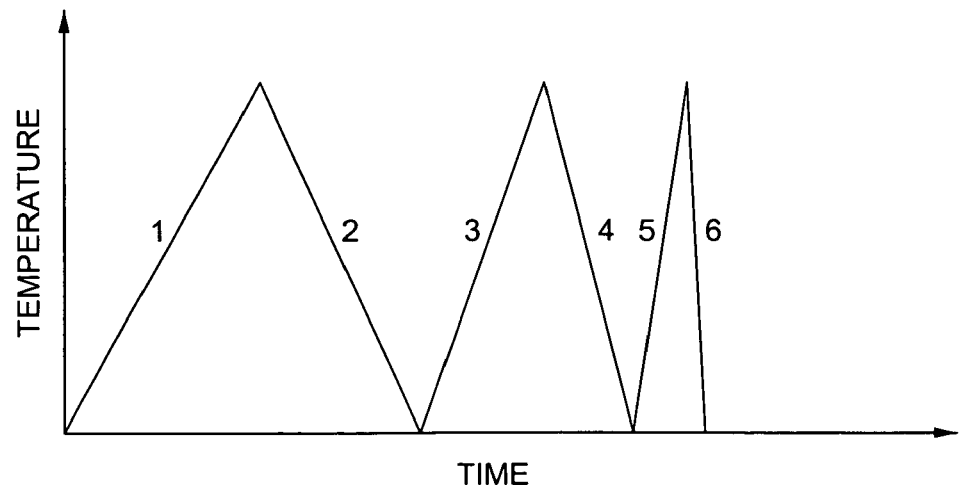
FIG. 3 is a plot of crystal temperature cycles of varying temperature gradients in accord with the invention.

In the two-dimensional approach of the invention, a crystal is subjected to a series of temperature T cycles 1, 2, 3, 4, 5, 6 of varying temperature rates, as shown in FIG. 3. During these cycles the state of the crystal can be considered as going through the curve shown in FIG. 4 on a plot of temperature T versus temperature rate $\dot{T}$ for a simple case where the heating and cooling rates are the same. Looking at temperature cycle 1 in FIG. 3, the temperature is increasing at a constant rate (e.g. 20 degrees/hour), thus the corresponding curve 1

Figure 4:
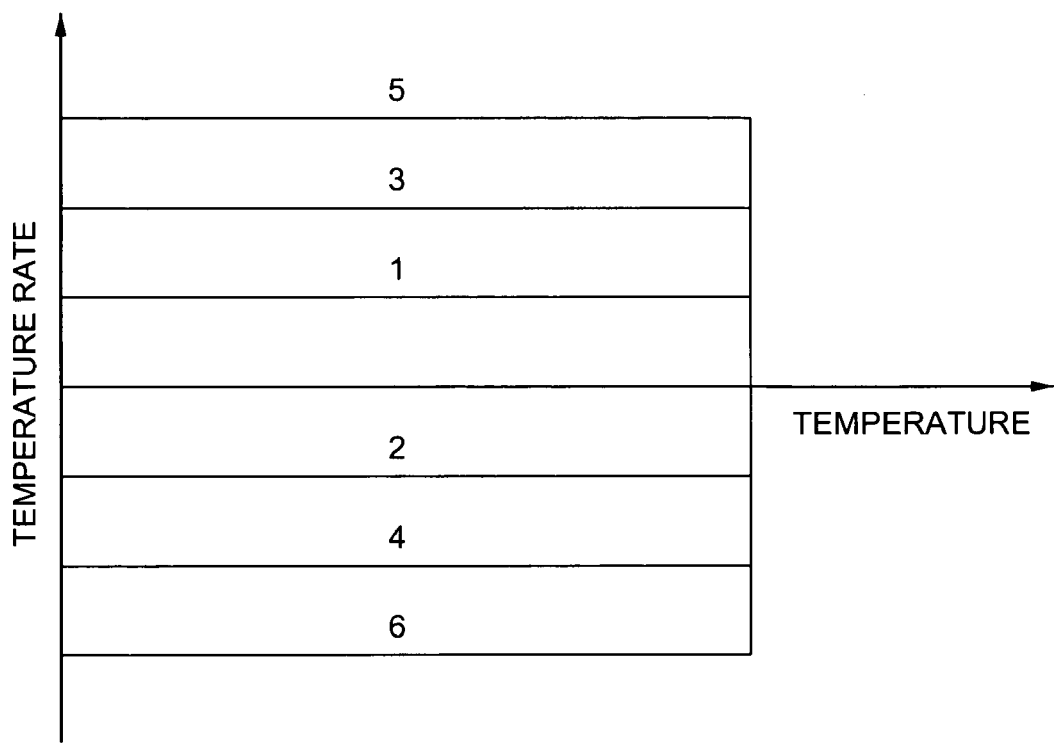
FIG. 4 is a plot of the temperature and temperature gradients of FIG. 3.

(rate T')

in FIG. 4 is a positive constant as the temperature T increases. In the cooling cycle 2, curve 2 (FIG. 4) remains constant as the temperature T decreases, but it is now a negative rate. For the next cycle 3, the temperature rate is higher as represented by curve 3 in FIG. 4, and so forth.

As the crystal 14 is subjected to the temperature cycles, the frequency, temperature parameter, and temperature rate are monitored and recorded. This characterization data can be graphed to define the shape of a surface within Cartesian three-dimensional space using a standard mathematical function of two real variables which assigns a unique real number or point z=f(x, y) to each ordered pair (x, y) of real numbers in the recorded data set. In this case, the ordered pair consists of the monitored temperature parameters T and temperature rates $\dot{T}$.

Figure 5:
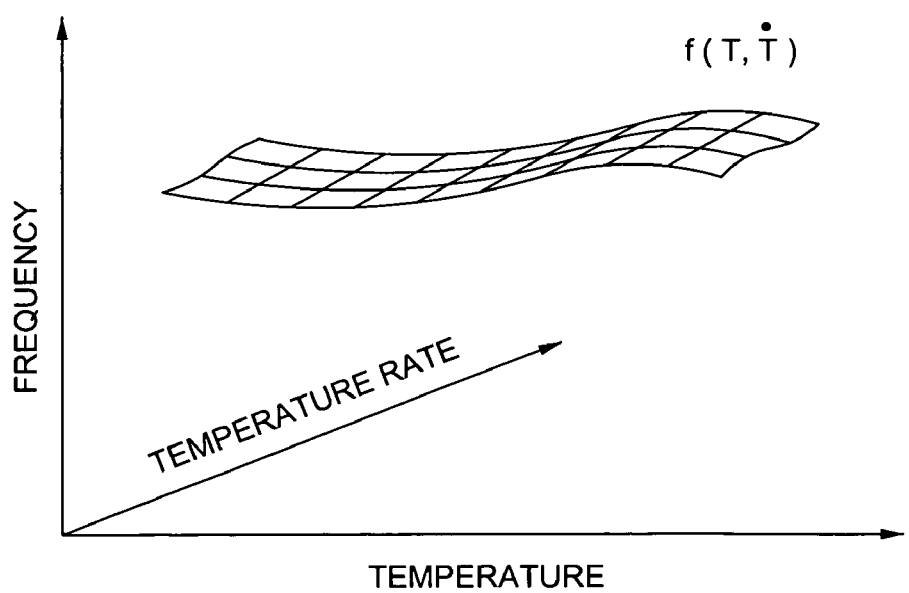
FIG. 5 is a plot of crystal frequency as a function of temperature and temperature rate depicted as a surface within Cartesian 3-D space.

As shown in FIG. 5, the crystal frequencies can be pictured as a set of points $(T,\dot{T})$ in the xy plane and the graph of the frequency function as the surface $f=f(T,\dot{T})$.

Thus as the point $(T,\dot{T})$ varies in the data set domain, the corresponding point (x, y, z)=

$(T,\dot{T},f(T,\dot{T}))$ varies over the surface. Any suitable software may be used to process the data set and plot the surface as known in the art. Interpolation or extrapolation techniques known in the art may be used to derive missing points in the surface $f=f(T,\dot{T})$.

Figure 6:
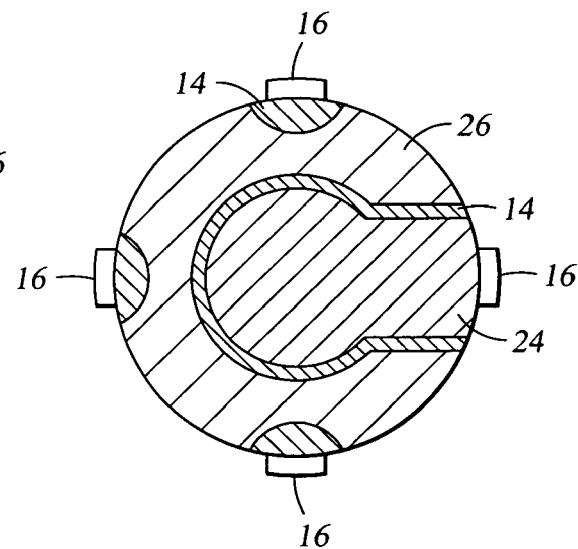
FIG. 6 is an overhead view of a quartz crystal in accord with the invention.

Once the surface is generated, it can be used in real time to compute the frequency more accurately by computing the temperature parameter T and temperature rate $\dot{T}$ Undesired gradient effects can also be reduced or eliminated by making the crystal 14 temperature distribution more uniform. FIG. 6 shows another embodiment of the invention. In this embodiment a dummy plating 26 is disposed on the quartz disc 14 surface to improve heat conduction across the disc. One or both sides of the disc 14 may be equipped with the plating 26. Any suitable heat conductor may be used for the plating 26 material (e.g. metal, which is good heat conductor). The plating 26 may be disposed on the disc 14 via any suitable means known in the art (e.g. electroplating, vapor deposition, etching, adhesives, etc.). Sufficient clearance should be left between the dummy plating 26, the mounting clips/leads 16, and the electrodes 22, 24 to prevent electrical shorts. Some embodiments may be implemented with bigger electrodes 22, 24 to cover a larger portion of the quartz disc 14 surface (not shown).

It will be appreciated by those of ordinary skill in the art that the present invention is applicable to, and can be implemented in, any field where quartz crystal oscillators are used as frequency standards (e.g. in apparatus for use in outer space, automobiles, etc.). While not limited to any particular application, the present invention is suitable for subsurface applications, where rapid temperature variations are encountered.

Figure 7:
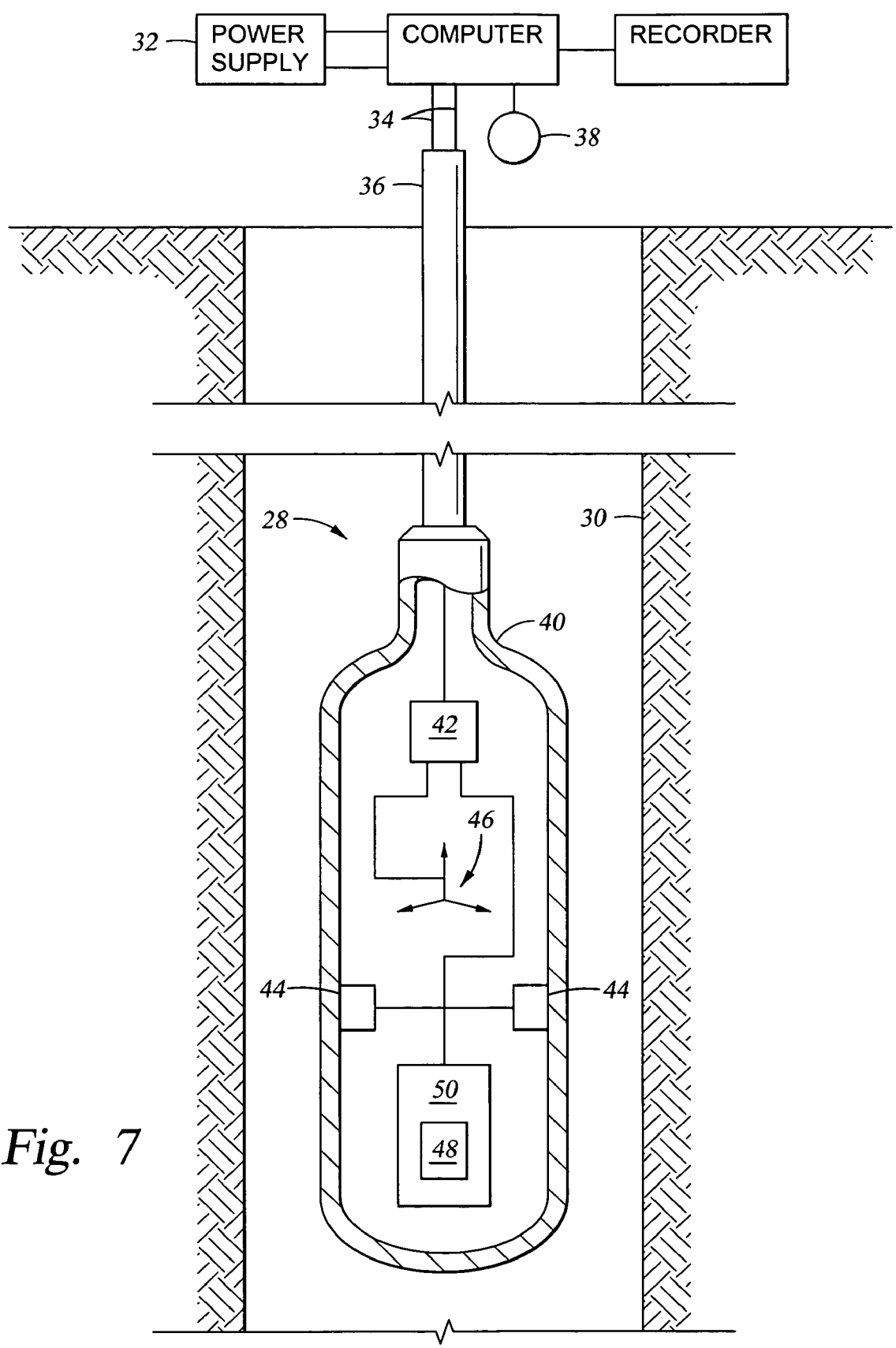
FIG. 7 shows a downhole logging system disposed in a borehole and equipped with a crystal oscillator in accord with the invention.

FIG. 7 shows another embodiment of the invention. A quartz crystal oscillator 48 is shown mounted in a downhole logging tool 28 disposed in a borehole 30 that penetrates an earth formation. The oscillator 48 is housed within a thermally insulated chamber 50 to reduce heat flow to the crystal during heating and cooling. The chamber 50 provides thermal insulation through the use of conventional insulating materials or by using a dewar flask as known in the art and described in U.S. Pat. No. 6,606,009. The tool 28 also includes a multi-axial electromagnetic antenna 19, a conventional source/sensor 44 array for subsurface measurements (e.g., nuclear, acoustic, gravity), and electronics 42 with appropriate circuitry. The tool 28 is shown supported in the borehole 30 by a logging cable 36 in the case of a wireline system or a drill string 36 in the case of a while-drilling system. With a wireline tool, the tool 28 is raised and lowered in the borehole 30 by a winch 38, which is controlled by the surface equipment 32. Logging cable or drill string 36 includes conductors 34 that connect the downhole electronics 42 with the surface equipment 32 for signal and control communication. Alternatively, these signals may be processed or recorded in the tool 28 and the processed data transmitted to the surface equipment 32.

It will also be apparent to those skilled in the art that this invention may be implemented by programming one or more suitable general-purpose microprocessors. The programming may be accomplished through the use of one or more program storage devices readable by the processor and encoding one or more programs of instructions executable by the processor for performing the operations described above. The program storage device may take the form of, e.g., one or more floppy disks; a CD ROM or other optical disk; a magnetic tape; a read-only memory chip (ROM); and other forms of the kind well-known in the art or subsequently developed. The program of instructions may be "object code," i.e., in binary form that is executable more-or-less directly by the processor; in "source code" that requires compilation or interpretation before execution; or in some intermediate form such as partially compiled code. The precise forms of the program storage device and of the encoding of instructions are immaterial here. Thus these processing means may be implemented in the surface equipment 32, in the tool 28, or shared by the two as known in the art.

Figure 8:
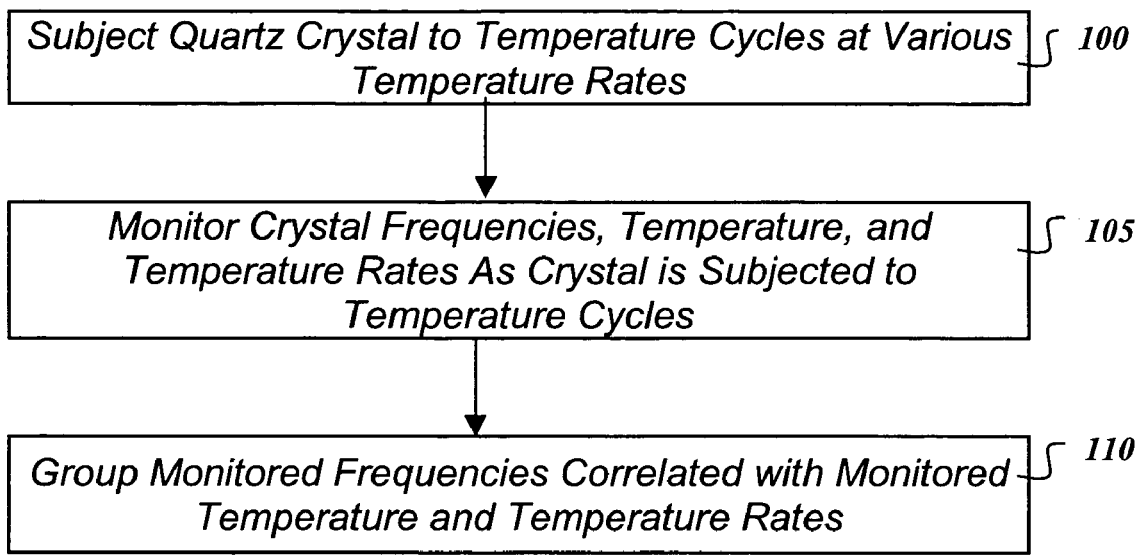
FIG. 8 illustrates a flow chart of a process for determining a frequency profile of a quartz crystal oscillator in accord with the invention.

An embodiment of the invention relates to a process for determining a frequency profile of a quartz crystal. FIG. 8 outlines the process. First the quartz crystal is subjected to temperature cycles at various temperature rates (step 100). This step may be performed during manufacture of the crystal or at any suitable location (e.g., a laboratory, a field location, etc.). Next, the crystal frequencies, a crystal temperature parameter, and the temperature rates are monitored as the crystal is subjected to the temperature cycles (step 105). Then a grouping is done of the monitored frequencies correlated with the monitored temperature parameters and temperature rates (step 110). The data grouping may be performed using processor means or any other suitable means known in the art.

Figure 9:
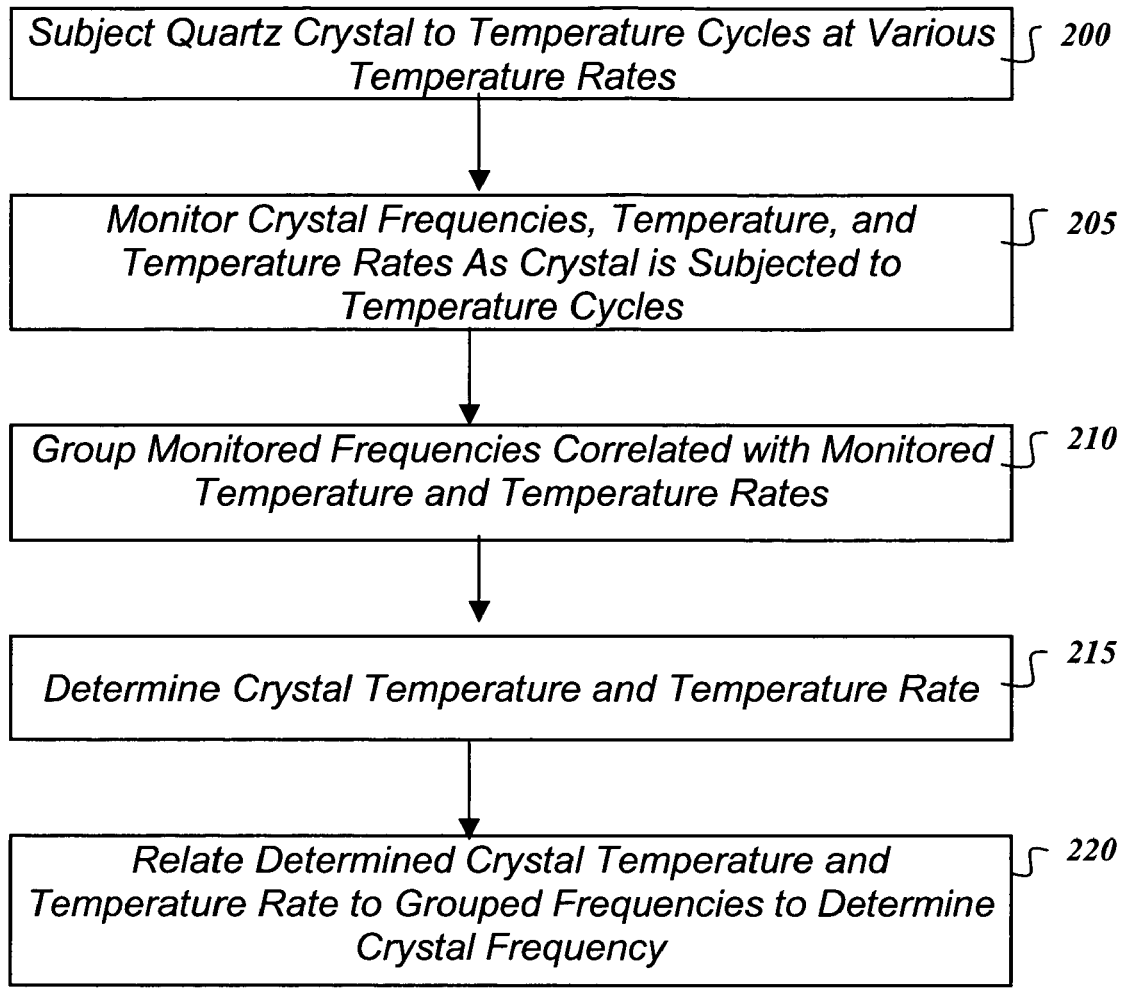
FIG. 9 illustrates a flow chart of a process for determining a frequency of a quartz crystal oscillator in accord with the invention.

FIG. 9 is a flow chart illustrating a process for determining a frequency of a quartz crystal according to the invention. The process begins by subjecting the quartz crystal to temperature cycles at various temperature rates (step 200). At step 205, the crystal frequencies, a crystal temperature parameter, and the temperature rates are monitored as the crystal is subjected to the temperature cycles. Then the monitored frequencies correlated with the temperature parameters and temperature rates are grouped (step 210). At step 215, the crystal temperature and a temperature rate of the crystal are determined. The temperature and rate determination is performed using any means known in the art and suitable for the particular environment. Finally, the determined crystal temperature and temperature rate are related to the grouped frequencies to determine the crystal frequency (step 220). This association is performed as described herein using microprocessor means or any other suitable means known in the art.

Figure 10:
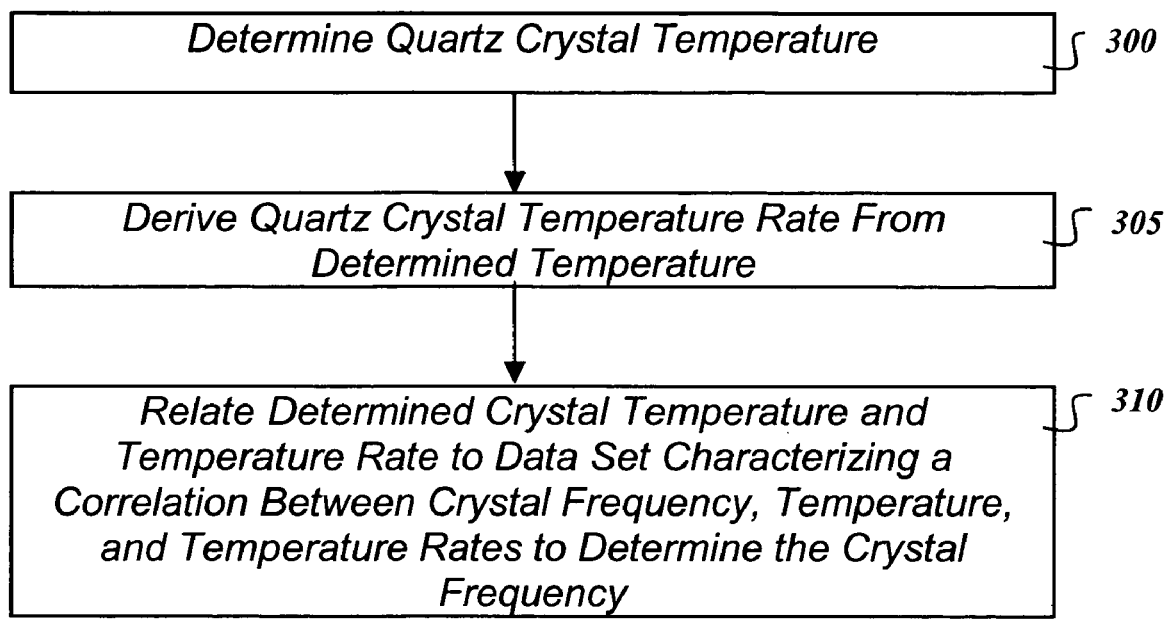
FIG. 10 illustrates a flow chart of a process for determining a frequency of a quartz crystal oscillator in real time in accord with the invention.

FIG. 10 is a flow chart illustrating a process for determining a frequency of a quartz crystal in real time according to the invention. The process begins by determining a temperature of the quartz crystal (step 300). The crystal temperature may be determined using any suitable means known in the art and appropriate for the particular crystal environment. A temperature rate is then derived from the determined crystal temperature (step 305). At step 310, the crystal frequency is determined by relating the crystal temperature and temperature rate to a data set characterizing a correlation between the crystal frequency, temperature, and temperature rates. The data set is compiled as described herein. For the purposes of this specification it will be clearly understood that the word "comprising" means "including but not limited to", and that the word "comprises" has a corresponding meaning.

The invention claimed is:

1. A method for determining a frequency profile of a quartz crystal, comprising:
   a) subjecting the quartz crystal to temperature cycles at various temperature rates;
   b) monitoring the crystal frequencies, a crystal temperature parameter, and the temperature rates as the crystal is subjected to the temperature cycles;
   c) grouping the monitored frequencies correlated with the monitored temperature parameters and temperature rates; and
   d) characterizing the crystal frequency (f) as a function of the monitored temperature parameters and temperature rates according to $$f=f(T,\dot{T}),$$

where T is a temperature parameter and $$\dot{T}=\frac{dT}{dt}$$

2. The method of claim 1, further comprising:
   d) defining a surface in Cartesian three-dimensional space using the frequencies, temperature, and temperature rates.

3. The method of claim 2, wherein the frequencies are graphed on the Cartesian z-axis according to $$z=f(x,y),$$

where x is a temperature value and y is a temperature rate.

4. The method of claim 3, further comprising performing an interpolation or extrapolation technique to derive missing points on the surface.

5. The method of claim 1, further comprising:
   d) graphing the crystal frequency f=f(T,$\dot{T}$) to define a surface in Cartesian three-dimensional space.

6. The method of claim 5, further comprising performing an interpolation or extrapolation technique to derive missing points on the surface.

7. The method of claim 1, wherein the crystal temperature parameter is one of a ratio of frequencies representative of temperature or a temperature value.

8. The method of claim 1, wherein the crystal temperature parameter is a temperature dependent frequency.

9. A method for determining a frequency of a quartz crystal, comprising:
   a) subjecting the quartz crystal to temperature cycles at various temperature rates;
   b) monitoring the crystal frequencies, a crystal temperature parameter, and the temperature rates as the crystal is subjected to the temperature cycles;
   c) roupin the monitored frequencies correlated with the temperature parameters and temperature rates;
   d) characterizing the crystal frequency (f) as a function of the monitored temperature parameters and temperature rates according to $$f=f(T,\dot{T}),$$

where T is a temperature parameter and $$\dot{T}=\frac{dT}{dt};$$

e) determining the temperature and a temperature rate of the crystal; and
   f) relating the determined crystal temperature and temperature rate to the characterized frequencies to determine the crystal frequency.

10. The method of claim 9, wherein step (c) includes defining a surface in Cartesian three-dimensional space using the frequencies, temperature, and temperature rates.

11. The method of claim 10, wherein the crystal frequencies are graphed on the Cartesian z-axis according to $z=f(x,y)$, where x is a temperature parameter and y is a temperature rate.

12. The method of claim 11, further comprising performing an interpolation or extrapolation technique to derive missing points on the surface.

13. The method of claim 9, further comprising graphing the crystal frequency $f=f(T,\dot{T})$ to define a surface in Cartesian three-dimensional space.

14. The method of claim 13, further comprising performing an interpolation or extrapolation technique to derive missing points on the surface.

15. The method of claim 9, wherein step (d) includes determining the crystal temperature when the crystal is located subsurface.

16. The method of claim 15, wherein the crystal is disposed in a tool adapted for subsurface disposal.

17. The method of claim 9, wherein the crystal temperature parameter is one of a ratio of frequencies representative of temperature or a temperature value.

18. The method of claim 9, wherein the crystal temperature parameter is a temperature dependent frequency.

19. A method for determining a frequency of a quartz crystal disposed in a tool adapted for subsurface disposal, comprising:
   a) determining a temperature of the quartz crystal in said tool;
   b) deriving a temperature rate from the determined crystal temperature; and
   c) relating the crystal temperature and temperature rate to a data set characterizing a correlation between grouped crystal frequencies (f), temperature, and temperature rates to determine the crystal frequency according to $f=f(T,\dot{T})$, where T is a temperature parameter and $$\dot{T} = \frac{dT}{dt}.$$

20. The method of claim 19, wherein the data set comprises a surface graphed in Cartesian three-dimensional space.

21. The method of claim 19, wherein the crystal frequency is determined in real time after determination of the crystal temperature.

22. The method of claim 21, wherein the crystal temperature is determined when the crystal is located subsurface.

23. A system for determining the frequency of a quartz crystal, comprising:
   a quartz crystal having a frequency output related to a temperature of the crystal; and
   a processor adapted to calculate a crystal frequency from a measured temperature parameter of the crystal, a temperature rate of the crystal, and observed frequencies of the crystal grouped with observed temperature parameters and temperature rates of the crystal;
   wherein the processor is adapted to characterize a relationship between the crystal frequency (f) and the observed temperature parameters and temperature rates according to $f=f(T,\dot{T})$, where T is a temperature parameter and $$\dot{T} = \frac{dT}{dt}.$$

24. The system of claim 23, wherein the processor is adapted to perform an interpolation or extrapolation technique to derive the crystal frequency.

25. The system of claim 23, wherein the measured crystal temperature parameter is determined for a crystal located subsurface.

26. The system of claim 25, wherein the crystal is disposed in a tool adapted for subsurface disposal.

27. The system of claim 23, wherein the observed frequencies, temperature parameters, and temperature rates of the crystal form a data set in a storage device operatively coupled to the processor.

28. The system of claim 23, wherein the crystal is disposed within a thermally insulated chamber.

29. The system of claim 23, wherein the crystal is adapted with a heat conducting material on its surface.

30. The system of claim 23, wherein the crystal temperature parameter is one of a ratio of frequencies representative of temperature or a temperature value.

31. The system of claim 23, wherein the crystal temperature parameter comprises a number of counts of a temperature dependent frequency mode.

* * * * *